(12) United States Patent
Killinger et al.

(10) Patent No.: US 7,755,041 B2
(45) Date of Patent: Jul. 13, 2010

(54) OPTICAL AND LASER DIFFERENTIAL ABSORPTION REMOTE DETECTION OF TATP PEROXIDE BASED EXPLOSIVES

(75) Inventors: Dennis K. Killinger, Temple Terrace, FL (US); Michael Sigman, Orlando, FL (US); Michael Maston, Oak Ridge, TN (US); Keith Williams, Edgefield, SC (US)

(73) Assignees: University of South Florida, Tampa, FL (US); University of Central Florida Research Foundation, Orlando, FL (US); NEWTEC Service Group, Inc., Edgefield, SC (US)

( * ) Notice: Subject to any disclaimer, the term of this patent is extended or adjusted under 35 U.S.C. 154(b) by 0 days.

(21) Appl. No.: 11/560,192

(22) Filed: Nov. 15, 2006

(65) Prior Publication Data

US 2007/0210254 A1 Sep. 13, 2007

Related U.S. Application Data

(60) Provisional application No. 60/597,179, filed on Nov. 15, 2005.

(51) Int. Cl.
 *B01D 59/44* (2006.01)
(52) U.S. Cl. .................................... 250/300
(58) Field of Classification Search ................. 250/300, 250/461.1, 573, 574, 221, 221.1, 338.5, 339.13; 702/28; 340/540; 436/172; 356/437, 301
 See application file for complete search history.

(56) References Cited

U.S. PATENT DOCUMENTS

| | | | |
|---|---|---|---|
| 6,522,402 B1 * | 2/2003 | Wang et al. | 356/327 |
| 6,750,467 B2 * | 6/2004 | Tulip | 250/573 |
| 6,822,742 B1 * | 11/2004 | Kalayeh et al. | 356/437 |
| 6,967,612 B1 * | 11/2005 | Gorman et al. | 342/22 |
| 2002/0014974 A1 * | 2/2002 | Ghahramani | 340/815.4 |
| 2002/0131463 A1 * | 9/2002 | Bruno et al. | 372/45 |
| 2004/0051867 A1 * | 3/2004 | Brestel et al. | 356/318 |
| 2004/0053421 A1 * | 3/2004 | Nguyen et al. | 436/172 |

(Continued)

OTHER PUBLICATIONS

Killinger et al., "Remote probing of the atmosphere using a CO2 DIAL system", 1981 IEEE, Journal of Quantum Electronics, vol. QE-17, No. 9, Sep. 1981.*

(Continued)

*Primary Examiner*—David P Porta
*Assistant Examiner*—Kiho Kim
(74) *Attorney, Agent, or Firm*—Jeremy Spier; Smith & Hopen, P.A.

(57) ABSTRACT

A triacetone triperoxide cloud associated with a triacetone triperoxide explosive attached to a hard target is remotely detected by operating differential-absorption lidar lasers to transmit a laser beam toward the hard target at differing wavelengths. A backscattered laser beam reflected from the lidar target (hard target, person, aerosols, clouds, buildings) is detected because a cloud of triacetone triperoxide in front of the lidar target and between the lidar target and the differential-absorption lidar system produces a differential-absorption signal having characteristics that identify the triacetone triperoxide. In a second embodiment, a triacetone triperoxide cloud that is absorbing optical radiation from its ambient environment and which is attached to a hard target is detected from a location remote from the triacetone triperoxide explosive by detecting an optical radiation absorption signature characterized by triacetone triperoxide absorption lines.

10 Claims, 6 Drawing Sheets

U.S. PATENT DOCUMENTS

2004/0155202 A1* 8/2004 Poteet et al. ............. 250/461.1
2007/0056388 A1* 3/2007 Henry et al. ............. 73/863.12

OTHER PUBLICATIONS

Primera-Pedrozo et al., "Use of fiber optic coupled FT-IR in detection of explosives on surfaces," 2004, the Proceedings of SPIE, pp. 237-245.*

Harper et al., "Identification of dominant odor chemicals emanting from explosives for use in developing optimal training and combinations and mimics for canine detection," 2005, Talanta, vol. 67, pp. 313-327.*

Vaicikauskas et al., "Infrared DIAL system for remote sensing of hazardous chemical agents," 2004, SPIE Proceedings, vol. 5613, pp. 21-28.*

* cited by examiner

OPTICAL AND LASER DIFFERENTIAL ABSORPTION REMOTE DETECTION OF TATP PEROXIDE BASED EXPLOSIVES

CROSS REFERENCE TO RELATED APPLICATIONS

This application claims priority to currently pending U.S. provisional patent application No. 60/597,179 by the same inventors, entitled "Laser Remote Detection of TATP Explosives," filed Nov. 15, 2005.

STATEMENT OF GOVERNMENT INTEREST

This invention was made with U.S. government support under Grant No. N66001-05-C-8017 (2005) awarded by DARPA/SPAWAR, under a contract from Newtek Corporation to the University of Central Florida to Dennis Killinger (Consultant, University of South Florida), and by a DARPA grant to the University of South Florida through US AFOSR FA9550-06-1-0363. The U.S. government has certain rights in the invention.

BACKGROUND OF THE INVENTION

1. Field of the Invention

This invention relates to laser remote sensing. More particularly, it relates to the remote detection and measurement of selected gases in the atmosphere or of trace gases emitted into the atmosphere.

2. Description of the Prior Art

The most common technique employed for laser remote sensing involves differential-absorption lidar (DIAL). DIAL transmits two or more different wavelengths toward a distant target and detects backscattered light using a telescope and optical detector. The technique of DIAL for the detection of trace gas clouds in the atmosphere has been known for many years.

Successful detection of a trace gas cloud requires that the gas being detected has a strong optical absorption of one of the DIAL laser wavelengths, and that lasers exit at the trace gas absorption wavelengths to permit DIAL or lidar detection of the backscattered optical signal. Previous attempts to detect gas clouds emitted by common nitrogen-based munitions explosives such as TNT and RDX have not been successful because the vapor pressure of TNT and RDX is extremely low. Attempts to use a DIAL remote sensing system were not successful because the optical depth (i.e., gas concentration times the optical attenuation coefficient of the gas) was negligible or very small. The remote detection of triacetone triperoxide (TATP) explosives had not yet been conducted successfully. It was not previously known that TATP had a high vapor pressure and strong optical absorption spectra that could be thus used for remote optical or DIAL detection of a TATP gas cloud.

Thus there is a need to incorporate DIAL technology into a system for remotely detecting the presence of TATP.

However, in view of the art considered as a whole at the time the present invention was made, it was not obvious to those of ordinary skill in this art how the identified needs could be met.

SUMMARY OF INVENTION

The long-standing but heretofore unfulfilled need for a method for detecting a TATP explosive from a safe, remote distance is now provided by a new, useful], and nonobvious invention.

The novel method for detecting a TATP cloud associated with a triacetone triperoxide explosive attached to a hard target, such as a person, from a location remote from said TATP explosive, includes the steps of operating a differential-absorption lidar system including differential-absorption lidar lasers to transmit a laser beam toward the hard target at differing wavelengths. A backscattered laser beam reflected from the hard target is then detected. The detection is possible because a cloud of triacetone triperoxide in front of the hard target and between the hard target and the differential-absorption lidar system produces a differential-absorption signal having characteristics that identify the triacetone triperoxide.

More particularly, the novel method includes the step of operating a line tunable $CO_2$ laser near 10.2 to 10.6 micron wavelength. The novel method also includes the step of operating a tunable quantum cascade laser near 8.2 micron wavelength or the step of operating a quantum cascade laser near 3.3 micron wavelength. Alternatively, the novel method can be performed by operating an optical parametric oscillator laser near 3.3 micron wavelength.

In a second embodiment of the novel method, a triacetone triperoxide cloud that is absorbing optical radiation from its ambient environment and which is attached to a hard target is detected from a location remote from the triacetone triperoxide explosive by detecting an optical radiation absorption signature characterized by triacetone triperoxide absorption lines or absorption bands.

Such detection may be performed by a spectroscopic instrument capable of detecting said absorption of optical radiation. A passive spectrometer or an imaging hyperspectral Fourier Transform-Infrared (FT-IR) instrument may also be used. An optical filtered spectroscopic imaging means that can detect the strong absorption features of triacetone triperoxide may also be employed.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
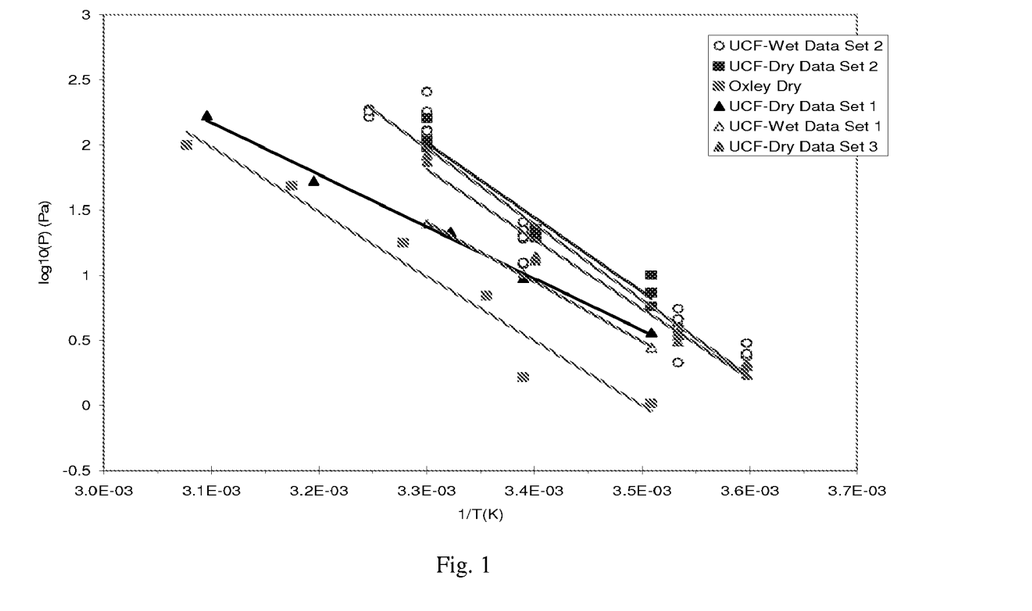
FIG. 1 is a graphical depiction of the vapor pressure of TATP.
Figure 2:
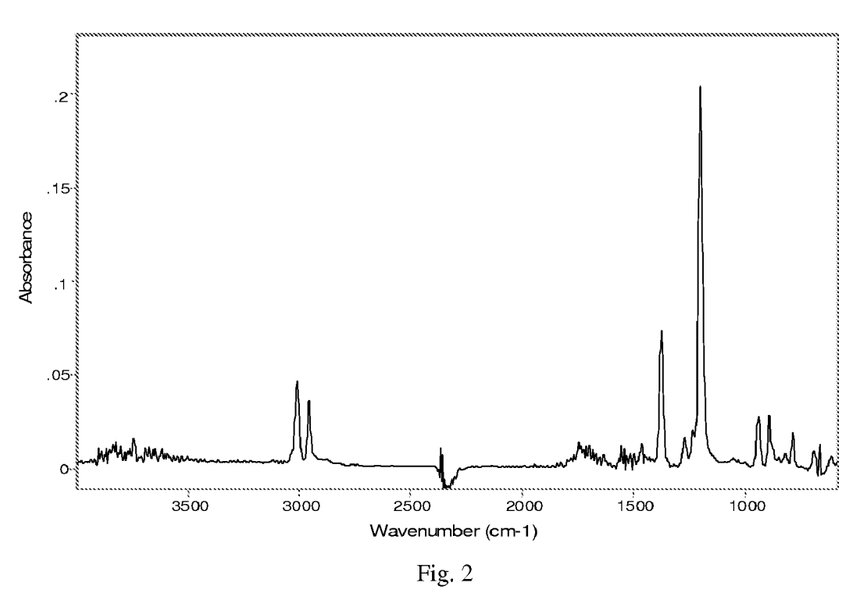
FIG. 2 is a graphical depiction of the optical absorption spectrum as a function of optical frequency (wavenumber, $cm^{-1}$) measured for TATP vapor showing the presence of strong absorption lines.
Figure 3:
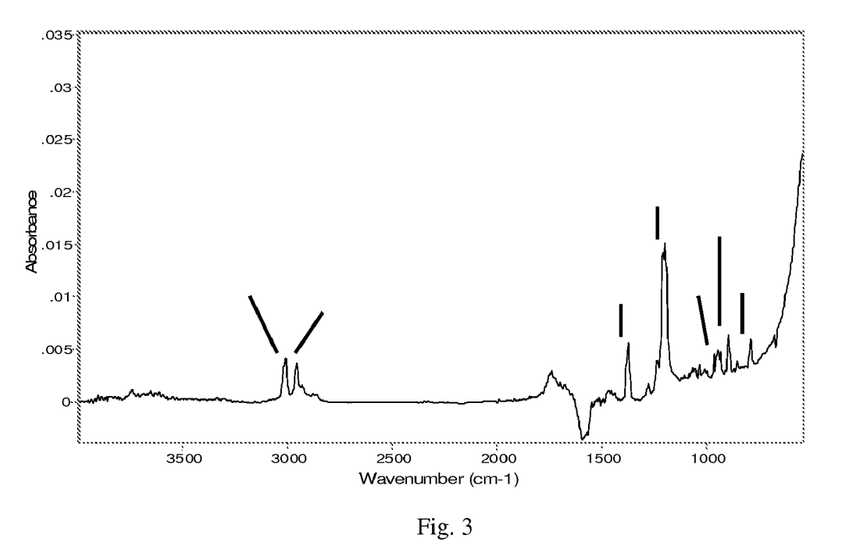
FIG. 3 is a graphical depiction of the optical absorption spectrum measured for TATP vapor showing the presence of strong absorption lines where the temperature and pressure in a five centimeter (5 cm) cell is 28° C. and 6.87 Pa (0.623 ng/mL), respectively.

A particular type of explosive, triacetone triperoxide (TATP), a peroxide-based explosive, has a vapor pressure that is fifteen thousand (15,000) times greater than that of TNT as graphically depicted in FIG. 1 and has large optical absorption spectral features as graphically depicted in FIGS. 2 and 3. More particularly, the vapor pressure of TATP is seven pascals (7 Pa), 0.05 torr, or 65 ppm.

Measurements conducted using actual samples of TATP indicates that the surrounding vapor cloud of TATP has a diameter of about one meter (1 m). A TATP-based explosive can be made easily and is unique in that it out gases readily.

The vapor cloud surrounding a solid sample of TATP could potentially produce an optical absorption of a transmitted optical beam of nearly 20% to 30% with the following values:

For a one meter (1 m) diameter cloud of TATP (twenty (20) times the length of a five centimeter (5 cm) cell×2-ways)

3010 $cm^{-1}$ (3.3 micron wavelength) line: Trans=0.69 or 31% absorption

1196 $cm^{-1}$ (8.2 micron wavelength) line: Trans=0.27 or 73% absorption

944 $cm^{-1}$ (10.6 micron wavelength) line: Trans=0.83 or 17% absorption

Such a large absorption signal is easily detected by a DIAL system or an optical spectroscopic detection instrument or a spectrometer imaging instrument such as the US Army M-21 FT-IR spectral detection passive spectroscopic system.

Lasers operating near the spectral absorption bands of TATP are available and such lasers are hereby identified for use in a laser remote sensing system for TATP detection. The lasers that may be used include a line tunable $CO_2$ laser operating near 10.2 to 10.6 micron wavelength, a tunable quantum cascade laser operating near 8.2 micron wavelength, and a quantum cascade laser or optical parametric oscillator (OPO) laser operating near 3.3 micron wavelength or frequency mixed or generated laser radiation at any of the three or more large absorption lines of TATP including those near 10.6 microns, 8.2 microns, and 3.3 microns. All three (3) of these lasers have been used in DIAL systems for remote detection of trace species in the atmosphere before, but have never been used for remote detection of TATP.

The preferred method of detection is where the TATP sample is contained within a package or person, and the TATP is out gassing sufficiently to produce a cloud of TATP (65 ppm concentration) in front of the container or person. The DIAL system transmits an eye-safe laser beam toward the person and detects the backscattered laser beam reflected from the hard target (person). The cloud of TATP in front of the person and between the hard target and the DIAL system produces the differential-absorption signal as the DIAL lasers are tuned or operated at the different DIAL wavelengths. The DIAL or Lidar target producing the backscattered DIAL or Lidar returns can also include aerosols, clouds, vapors, or hard targets such as buildings, person, car bodies, and trees.

In a second embodiment, the TATP cloud absorbs ambient light from the sun, moon, environment, thermal radiation, or the like and produces an absorption signature due to the TATP absorption lines. This absorption of optical radiation can be detected by different types of spectroscopic instruments, including a passive spectrometer, an imaging hyperspectral FT-IR instrument, or optical filtered spectroscopic imaging CCD camera or detector that can detect the strong optical absorption features of TATP.

The vapor pressure of TATP was found to be 15,000 times higher than most other explosives. The measured vapor pressure of TATP obtained by the inventors is disclosed in FIG. 1. The vapor pressure is high for TATP because it evaporates at a very fast rate (approximately five per cent (5%) of its weight within a few days).

The measured absorption optical spectrum of TATP vapor as a function of optical frequency ($cm^{-1}$) (obtained by the inventors) is very large, as graphically depicted in FIGS. 2 and 3, and can be used for detection of TATP clouds.

In the graphical depiction of FIG. 3, the strong optical absorption due to TATP is seen near 3.3 microns, 8.2 microns and 10.6 microns.

Figure 4:
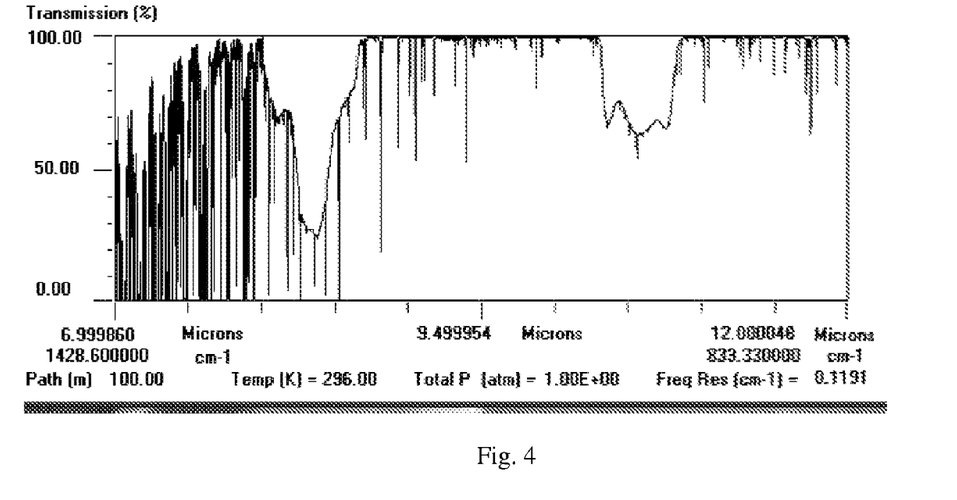
FIG. 4 is a graphical depiction of the 2-way transmission spectrum of the atmosphere (100 m path) with the addition of a one meter (1 m) diameter cloud of ambient vapor pressure (6.87 Pa) TATP.

A DIAL parameter study indicates that the absorption spectrum of TATP is readily observable against the spectrum of the atmosphere. FIG. 4 depicts the superimposed spectrum of a 1-m diameter cloud of TATP with that of the ambient atmosphere (path length of 100 m).

DIAL calculations (FIG. 5) indicate that a TATP cloud associated with a TATP explosive sample is detectable at ranges up to four hundred meters (400 m).

$CO_2$ lasers have the appropriate tuning range to provide off-line (10.2 micron; not absorbed) and on-line (10.6 micron; absorbed) wavelengths for DIAL detection of TATP.

Quantum cascade lasers are tunable lasers and operate near 8.2 microns and 3.3 microns, and can be tuned on-line and off-line of the TATP absorption features.

Optical parametric oscillator lasers operate near 3.3 microns and near 8.2 microns and near 10.6 microns and can be used for TATP DIAL detection.

The strong optical absorption features of TATP near 3.3, 8.2, and 10.6 microns can be detected by using a FT-IR or other spectroscopic detection instrument that would measure the TATP absorption of natural sunlight or ambient lighting illuminating a target behind the TATP cloud or measuring the differential radiance of the thermal radiation absorbed by the TATP cloud compared to the thermal emission of the background scene.

Figure 5:
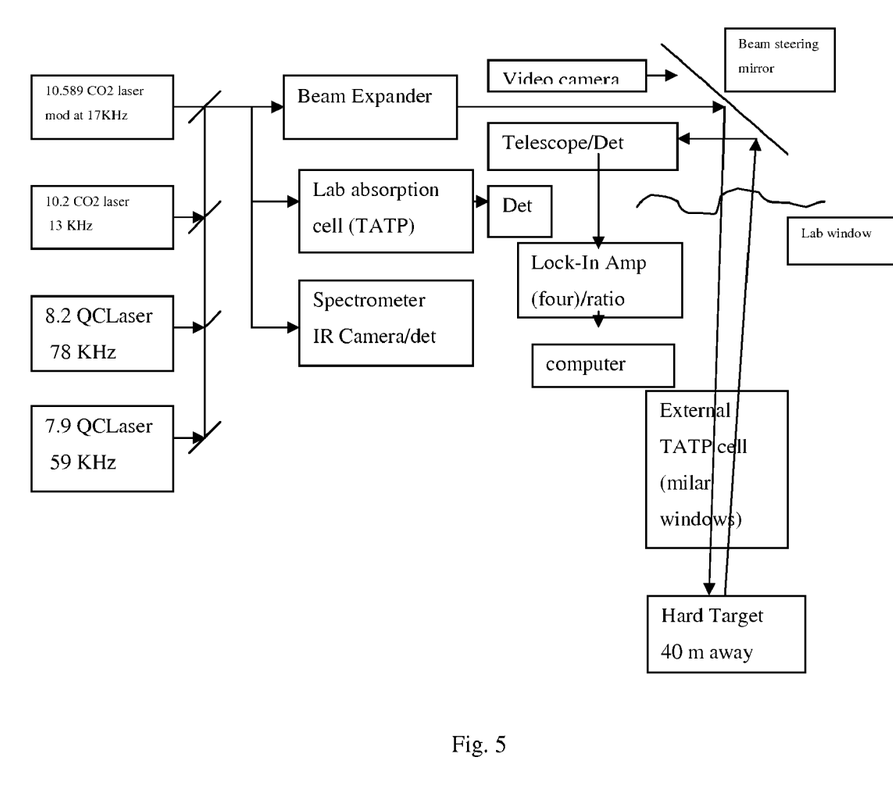
FIG. 5 is a diagrammatic representation of a DIAL system for remote detection of a TATP gas cloud.

FIG. 5 is a diagrammatic representation of a DIAL system for remote detection of a TATP gas cloud using either $CO_2$ lasers operating near 10.2 to 10.6 microns, or quantum cascade lasers operating near 8.2 microns or near 3.3 microns. Dual wavelength DIAL (such as 10.6 and 8.2 microns) may also be used to improve DIAL system sensitivity. In FIG. 5, TATP is contained within an optical absorption cell. The TATP would surround a remote TATP sample.

Figure 6:
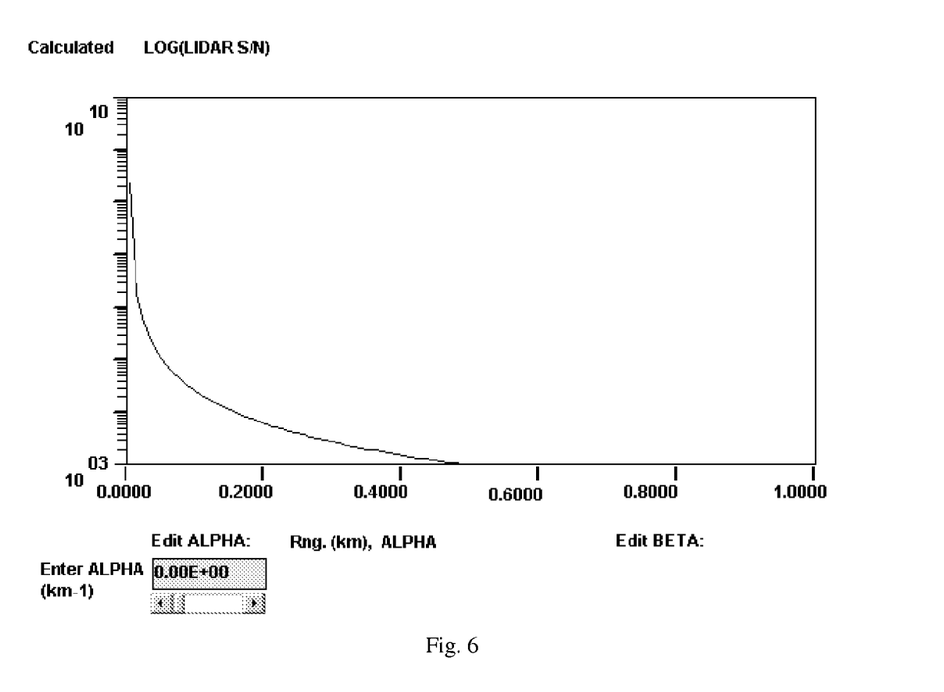
FIG. 6 graphically depicts a calculated DIAL signal-to-noise ratio for DIAL detection of TATP as a function of detection range.

FIG. 6 graphically depicts a calculated DIAL signal-to-noise ratio for DIAL detection of TATP as a function of detection range in kilometers.

Figure 7:
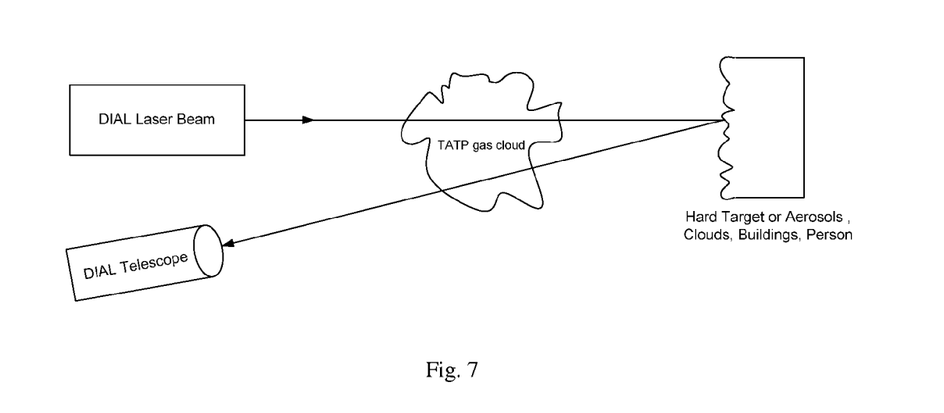
FIG. 7 is a schematic of the DIAL detection of a TATP gas cloud.

FIG. 7 graphically depicts remote detection of a TATP gas cloud using a DIAL system that uses backscattered laser radiation from hard targets or from aerosols, clouds, or vapors in the atmosphere.

Figure 8:
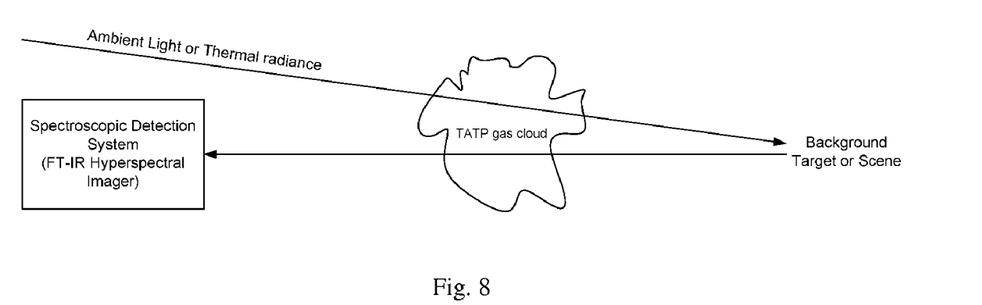
FIG. 8 is a schematic of the optical absorption spectroscopic detection of a TATP gas cloud.

FIG. 8 graphically depicts remote detection of a TATP gas cloud using a spectroscopic instrument (such as a FT-IR, hyperspectral imager, optical filtered CCD Camera) to detect the TATP optical absorption of ambient light or thermal emission.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for remotely detecting a triacetone triperoxide cloud having a large optical absorption coefficient (i.e., optical absorption cross section) associated with a triacetone triperoxide explosive attached to a person comprising the steps of:
    employing a differential-absorption lidar system including differential-absorption lidar lasers to transmit a laser beam toward the person;
    operating the differential-absorption lidar lasers at differing wavelengths during said transmission of said laser beam;
    detecting a backscattered laser beam reflected from the person;
    detecting a backscattered laser beam reflected from an atmospheric aerosol lidar target or atmospheric cloud lidar target; and
    detecting a cloud of triacetone triperoxide having a large optical absorption coefficient (i.e., optical absorption cross section) in front of the person and between the person and the differential-absorption lidar system by receiving a differential-absorption signal having characteristics that identify the triacetone triperoxide.

2. The method of claim 1, further comprising the step of:
    operating a line tunable $CO_2$ laser near 10.2 to 10.6 micron wavelength.

3. The method of claim 1, further comprising the step of:
    employing a tunable quantum cascade laser operating near 8.2 micron wavelength.

4. The method of claim 1, further comprising the step of:
    operating a quantum cascade laser near 3.3 micron wavelength.

5. The method of claim 1, further comprising the step of:
    operating an optical parametric oscillator laser or frequency mixed laser near 3.3 micron, 8.2 micron, or 10.6 micron wavelength.

6. A method for remotely detecting a triacetone triperoxide cloud having a large optical absorption coefficient (i.e., optical absorption cross section) associated with a triacetone triperoxide explosive attached to a person, said triacetone triperoxide cloud absorbing optical radiation from its ambient environment, comprising the steps of:
    operating a differential-absorption lidar laser having a wavelength near 3.3 microns, 7.3 microns, 8.2 microns, 10.6 microns, or 11.2 microns to transmit a laser beam toward said person;
    detecting an optical radiation absorption signature characterized by triacetone triperoxide's large absorption coefficient (i.e., optical absorption cross section).

7. The method of claim 6, further comprising the step of:
    employing a spectroscopic instrument to detect said absorption of optical radiation.

8. The method of claim 7, further comprising the step of employing a passive spectrometer.

9. The method of claim 7, further comprising the step of employing an imaging hyperspectral FT-IR instrument.

10. The method of claim 7, further comprising the step of:
    employing an optical filtered spectroscopic imaging CCD camera or IR imaging camera that can detect the strong absorption features of triacetone triperoxide.

* * * * *